United States Patent [19]

Watson et al.

[11] Patent Number: 5,059,533
[45] Date of Patent: Oct. 22, 1991

[54] RHIZOBIAL FERREDOXIN GENES

[75] Inventors: John M. Watson, Holder; Siiri E. Iismaa, Thirlmere, both of Australia; Helmut Reilander; Alfred Puhler, both of Bielefeld, Fed. Rep. of Germany; Hauke Hennecke, Zurich, Switzerland

[73] Assignee: Lubrizol Genetics, Inc., Wickliffe, Ohio

[21] Appl. No.: 219,738

[22] Filed: Jul. 15, 1988

Related U.S. Application Data

[63] Continuation-in-part of Ser. No. 19,043, Feb. 26, 1987.

[51] Int. Cl.$^5$ .................... C12N 15/00; C12P 21/00; C12R 1/41; C07H 15/12
[52] U.S. Cl. ................ 435/172.3; 435/69.1; 435/252.2; 435/878; 536/27; 935/9; 935/11
[58] Field of Search ............... 435/172.3, 320, 252.2, 435/878, 69.1; 536/27; 935/9, 11

[56] References Cited

PUBLICATIONS

Granger et al., 1987, Nucleic Acids Res. 15 (1):31–49.
Carter et al., 1980, J. Biol. Chem. 255(9): 4213–4223.
Graves et al., 1985, Proc. Natl. Acad. Sci. U.S.A., 82:1653–1657.
Dusha et al. (1987) J. Bacteriol. 169:1403–1409.
Iismaa, S. and Watson, J. M. (1987) Nucl. Acids Res. 15:3180.
Buikema, W. J. et al. (1987) J. Bacteriol. 169:1120–1126.
Noti, J. et al. (1986) J. Bacteriol. 167:774–783.
Ebeling, S. et al. (1988) J. Bacteriol. 170:1999–2001.
Minami et al. (1984) J. Biochem. 96:585–591.
Tanaka et al. (1974) Biochem. 13:2953–2959.

Primary Examiner—Elizabeth C. Weimar
Assistant Examiner—David T. Fox
Attorney, Agent, or Firm—Greenlee and Associates

[57] ABSTRACT

Rhizobial ferredoxin genes and proteins are provided. Rhizobial ferredoxins are useful to enhance the nitrogenase systems of rhizobia. Useful rhizobial ferredoxin diagnostic segments are also provided comprising DNA sequences encoding the characteristic ferredoxin cysteine residue patterns. Exemplified rhizobial ferredoxin genes are fixX of *Rhizobium trifolii* and *Rhizobium meliloti* Between fixC and nifA, fixY of *Rhizobium meliloti* down stream from nifB, and frxA of *Bradyrhizobium japonicum*.

4 Claims, 3 Drawing Sheets

RHIZOBIAL FERREDOXIN GENES

This application is a continuation-in-part of co-pending application Ser. No. 019,043, filed Feb. 26, 1987, which is incorporated herein by reference.

FIELD OF THE INVENTION

This invention relates to the field of recombinant DNA, and in particular to the isolation, characterization, and sequencing of rhizobial genes for the production of ferredoxins and ferredoxin-like proteins.

BACKGROUND OF THE INVENTION

Soil bacteria of the genus Rhizobium, a member of the family Rhizobiaceae, are capable of infecting plants and inducing a highly differentiated structure called the root nodule, within which atmospheric nitrogen is reduced to ammonia by the bacteria. The host plant is most often of the family Leguminosa. Previously, Rhizobium species were informally classified into two groups, "fast-growing" or "slow-growing," to reflect their relative growth rates in culture. The group of "slow-growing" rhizobia has recently been reclassified as a new genus, Bradyrhizobium (D.C. Jordan (1982) Int. J. Syst. Bacteriol. 32:136; *Bergey's Manual of Determinative Bacteriology*, Vol. I, 1984, Holt et al., eds). The fast-growing rhizobia include *Rhizobium trifolii, R. meliloti, R. leguminosarum*, and *R. phaseolus*. These strains generally display narrow host ranges. Fast-growing *R. japonicum* (now known as *R. fredii*) which nodulates wild soybean and *Glycine max* cv. Peking but forms ineffective nodules on commercial soybean cultivars, has also been described. These *R. japonicum* (*R. fredii*) strains, as well as fast-growing members of the cowpea Rhizobium (now *R. loti*), display a broader host range. The genus Bradyrhizobium includes the commercially important soybean-nodulating strains of *Bradyrhizobium japonicum* (i.e., USDA 110 and USDA 123) and the symbiotically promiscuous rhizobia of the "cowpea group." Also included is Bradyrhizobium sp. (Parasponia) (formerly Parasponia Rhizobium) which nodulates a number of tropical legumes including cowpea and siratro, and is distinguished by its ability to nodulate the non-legume Parasponia.

Nodulation, the development of effective symbiosis, and nitrogen fixation are complex processes requiring both plant and bacterial genes. Several reviews of the genetics of the Rhizobium-legume interaction are found in W. J. Broughton (ed.) (1982) *Nitrogen Fixation*, Volumes 2 and 3, Clarendon Press, Oxford; A. Puhler (ed.) (1983) *Molecular Genetics of the Bacteria-Plant Interaction*, Springer-Verlag, Berlin; A. Szalay and R. Legocki, (eds.) (1985) *Advances in Molecular Genetics of the Bacteria-Plant Interaction*, Cornell University Press, Ithaca, New York; S. Long (1984) in *Plant-Microbe Interaction* Volume I, T. Kosuge and E. Nester (eds.), McMillan, New York, pp. 265-306; and D. Verma and S. Long (1983) International Review of Cytology (Suppl. 14) K. Jeon (ed.), Academic Press, p. 211-245.

In the fast-growing species, the genes required for nodulation and nitrogen fixation are located on large Sym (symbiosis) plasmids. Such genes include those required for nodule initiation and development (nod), those genes which have a *Klebsiella pneumoniae* homologs (nif), such as the structural genes for nitrogenase (nifHDK) and the regulatory gene nifA, and other genes involved in nitrogen fixation (fix). A number of genes determining nodulation functions (nodEFDABC) and the nifHDK genes have been mapped on the 180 kb Sym plasmid of *R. trifolii* ANU843 (P. Schofield et al. (1983) Mol. Gen. Genet. 192:459; P. Schofield et al. (1984) Plant Mol. Biol. 3:3). Nodulation and nitrogenase genes have also been mapped to symbiotic plasmids in *R. leguminosarum* (Downie et al. (1983) Mol. Gen. Genet. 190:359) and in *R. meliloti* (Kondorosi et al. (1984) Mol. Gen. Genet. 193:445).

The nitrogenase and nodulation genes of *B. japonicum* and Bradyrhizobium sp. (Parasponia) are believed to be chromosomally encoded. Sym plasmids have not been found to be associated with nitrogen fixation in the slow-growing rhizobia. A review of the genetics of symbiotic nitrogen fixation in *B. japonicum* is given in H. Hennecke et al. (1987) in *Molecular Genetics of the Plant-Microbe Interaction*, D. Verma and N. Brisson (eds.), Martinus Nijhoff Publishers, The Netherlands, pp. 191-196.

Ferredoxins are cysteine-residue-containing non-heme iron-sulfur proteins which serve as electron carriers in a variety of metabolic reactions (R. Thauer et al. (1982) in *Iron Sulfur Proteins*, T. Spiro (ed.), pp. 329-341). Ferredoxins are found in a number of microorganisms as well as in plants such as spinach and parsley. A ferredoxin has been isolated from *Rhizobium japonicum* (now *Bradyrhizobium japonicum*) bacteroids of soybean root nodules (K. Carter et al. (1980) J. Biol. Chem. 255:4213). The authors report that the bacteroid ferredoxin is capable of functioning as an electron donor for nitrogenase in *R. japonicum* bacteroides. The amino acid composition but not the amino acid sequence of the ferredoxin protein was disclosed. Thus, Carter et al. presents no teaching suggestions which would lead the skilled artisan to the present invention. Genes encoding rhizobial ferredoxins have only recently been described in the literature.

There have been reports concerning the ferredoxin genes of some nitrogen-fixing bacteria other than Rhizobium. M. Graves et al. (1985) Proc. Nat. Acad. Sci USA 82:1653, reported the sequence of a *Clostridium pasteurianum* ferredoxin gene, but did not suggest a nitrogenase function for it. The in vitro transcription of the *C. pasteurianum* ferredoxin gene has also been described (M. Graves et al. (1986) J. Biol. Chem 261:11409). The first report of linkage between a structural gene for nitrogenase and a ferredoxin gene was in *Azotobacter chrococcum* (R. Robson et al. (1986) EMBO J. 5:1159). Those authors also provided the nucleotide sequence of the ferredoxin gene.

Nucleotide sequences for genes identified as rhizobial ferredoxins have only recently been disclosed in the literature. P. Gronger et al. (1987) Nucleic Acids Res. 15:31 (co-authored by the inventors of the parent application hereof, Ser. No. 019,043) presented an amino acid sequence corresponding to the fixX gene of *R. meliloti*, and DNA and amino acid sequences for the corresponding region of *R. leguminosarum*. The *R. leguminosarum* sequence did not contain the complete ferredoxin diagnostic pattern, and the article contained no teaching suggesting that those sequences encoded or comprised ferredoxins or were useful in nitrogenase systems. C. Earl et al. (1987) J. Bacteriol. 169:1127 disclosed the ferredoxin-like sequence of the gene called fixX from *R. meliloti* 1021. As reported therein, the existence of this sequence was disclosed to the authors by one of the co-inventors of the parent application hereof. Similarly, I. Dusha et al. (1987) J. Bacteriol.

169:1403–1409, in an article published after the filing date of said parent application, reported the existence of the fixX gene of *R. meliloti* 41 and that insertional inactivation of the fixX gene resulted in a Fix⁻ phenotype. The DNA and the deduced amino acid sequences of the fixX gene led the authors to the conclusion that fixX encoded a ferredoxin. The DNA sequence of a *R. trifolii* gene (termed fixX herein) and the deduced amino acid sequence of its ferredoxin-like gene product were disclosed in S. Iismaa and J. M. Watson (1987) Nucleic Acids Res. 15:3180, published after the filing data of the parent application hereof. The fixX genes of the present invention correspond to those designated "ORF1" in the parent application hereof. W. J. Buikema et al. (1987) J. Bacteriol. 169:1120–1126, in an article published after the filing date of the parent application hereof, noted that the deduced amino acid sequence of an open reading frame downstream of the *R. meliloti* nifB gene exhibited significant homology to the amino acid sequences of other bacterial ferredoxins; this open reading frame corresponds to the fixY gene of this application, and to ORF2 of the parent application hereof. J. Noti et al. (1986) J. Bacteriol. 167:774–783, disclosed the DNA sequence of nifB gene and about 81 bp downstream from the nifB stop codon. Within that sequence downstream of nifB is found the DNA encoding approximately the first 72 bp of the frxA gene of the present invention, including the sequence coding for the diagnostic ferredoxin pattern of cysteine residues. However, Noti et al. (supra) give no teaching suggesting that there is a ferredoxin-like gene in that segment of Bradyrhizobium DNA. Furthermore, this article teaches away from the present invention because Noti et al. proposed that downstream of nifB there is an 831 bp ORF, starting with an ATG translation initiation codon about 8 bp 3′ to the nifB stop codon. The work of the present invention teaches that the frxA ferredoxin gene is a 222 bp ORF which begins with a GTG translation initiation codon about 10 downstream of the nifB stop codon. Furthermore, the reading frame of frxA is different from that of the ORF disclosed in Noti et al. (supra). Information concerning frxA was disclosed in S. Ebeling et al. (1988) J. Bacteriol. 170:1999–2001, an article co-authored by one of the co-inventors of this application.

Ferredoxins are useful for in vitro photochemical hydrogen production (Kirk Othmer Chemical Encyclopedia; D. Arnon et al. (1961) Science 134:1425) and for other reactions requiring iron-sulfur proteins as electron carriers, as known to the art. K. Carter et al. (supra) reported numerous differences between the *R. japonicum* bacteroid ferredoxin and other bacterial ferredoxins. For example, the bacteroid ferredoxin is effective, in the photochemical reduction of acetylene but ineffective as a cofactor in the clostridial phosphoroclastic reaction. Both ferredoxins from *A. vinelandii* are effective in these reactions. Due to the differences in the redox conditions for the nitrogenase systems of different bacteria, a rhizobial ferredoxin should be used for rhizobial nitrogenase systems, either in vivo or in vitro.

It is therefore desirable to provide a method for the production of rhizobial ferredoxins for use in in vitro hydrogen generation systems and in nitrogenase systems involving rhizobial enzymes. It is also desirable to enhance rhizobial nitrogen fixation by improving electron transport through providing ferredoxin genes to such organisms either to replace defective genes or to add to pre-existing ferredoxin genes. It is also desirable to produce a rhizobial ferredoxin protein as the expression product of a rhizobial ferredoxin gene.

SUMMARY OF THE INVENTION

DNA sequences have been identified in *Rhizobium trifolii*, *Rhizobium meliloti*, and *Bradyrhizobium japonicum* as ferredoxin sequences. The ferredoxin sequences disclosed herein are known as fixX from *R. trifolii*, fixX from *R. meliloti*, fixY from *R. meliloti*, and frxA from *B. japonicum*. Analysis of these sequences shows their similarity with other rhizobial sequences. Other species having such sequences include, but are not limited to, *R. leguminosarum*, *R. phaseoli*, *R. fredii*, *R. loti*, and Bradyrhizobium sp. (Parasponia).

It was discovered that these rhizobial sequences encode proteins, each of which has the preferred pattern of cysteine residues of this invention (C--C--C---C) characteristic of ferredoxins in a number of bacterial species: *Clostridium* sp., *Desulfovibrio desulfuricans*, *Methanosarcina barkeri*, *Petococcus aerogenes*, *Megasphaera elsdenii*, *Clostridium tartarivorum*, *Pseudomonas putida*, *Azotobacter vinelandii*, *Mycobacterium smegmatis*, *Clostridium acidi-urici*, *Clostridium butyricum*, *Rhodospirillum rubrum*, *Clostridium pasteurianum*, *Thermus aquaticus*, and *Bacillus acidocaldarius*. (See database of protein sequences of Protein Identification Resource (NBRF).) Additionally, the amino acid sequence of fixY of *R. meliloti* showed further homologies to ferredoxins from *Chlorobium limicola*, *C. limicola. f, C. lim* 2, and *Azotobacter chrococcum*.

A rhizobial ferredoxin of this invention is a protein found in rhizobia having a cysteine residue pattern characteristic of bacterial ferredoxins and capable of functioning as an electron carrier in reactions of nitrogenase enzymes and related cofactors. The cysteine residue pattern consists of a cluster of three or four cysteine residues separated from each other by one to four intervening residues. The preferred cysteine residue pattern is a cluster of four cysteine residues with three neighboring cysteine residues each separated by two intervening residues and the fourth cysteine residue separated from the other three cysteine residues by three intervening residues (C--C--C--C---C). Particularly when the ferredoxin genes of this invention are used to enhance electron transport in *R. trifolii* or in *R. meliloti* nitrogenase systems, the preferred cysteine residue pattern should be used, as this is the pattern found in such organisms in nature. As is known to the art, the functional ferredoxin protein contains iron complexed to the sulfurs provided by the cysteine residues.

A rhizobial ferredoxin gene of this invention is a DNA sequence encoding a rhizobial ferredoxin, which sequence is found in rhizobia. A sequence which has at least 70% homology to a rhizobial ferredoxin gene and which encodes a ferredoxin functional in rhizobia, whether obtained from rhizobia, synthetic, mutated, or derived from non-rhizobial sources, is included within the definition of a "rhizobial ferredoxin gene." It is understood that a rhizobial ferredoxin gene will contain a sequence which encodes the cysteine residue pattern characteristic of ferredoxins.

Figure 1:
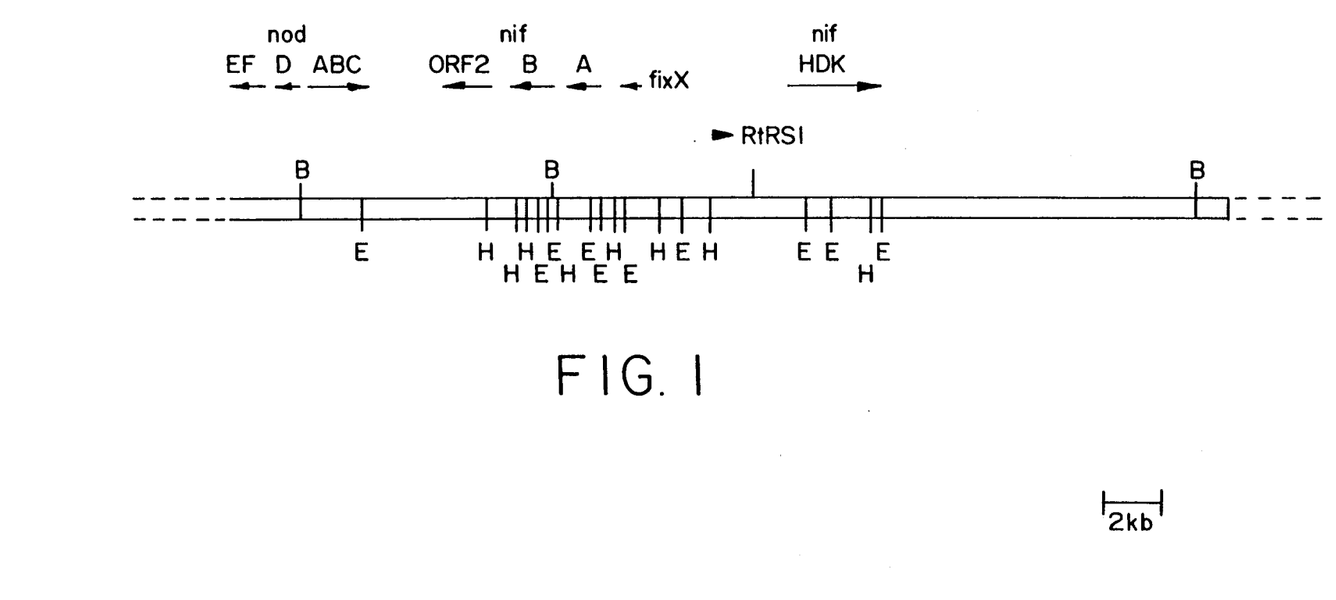
FIG. 1 is a Region Map showing the nod, nif, and fix genes of *R. trifolii*. H, E and B represent a HindIII, EcoRI and BamHI restriction sites, respectively. RtRS1 represents a repeating sequence comprising a nifH promoter.
Figure 2:
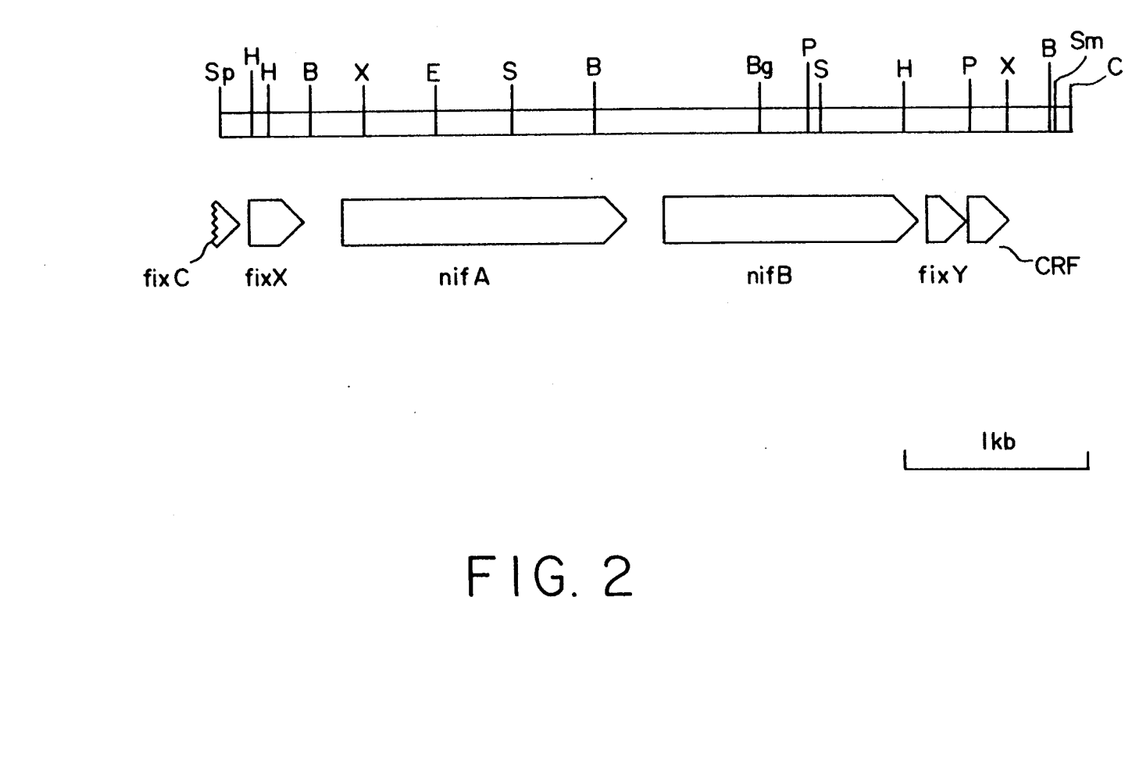
FIG. 2 shows the Region Map of the fix and nif genes of *R. meliloti*. H, B, P, S, Sm, Bg, X, Sp and C represent restriction endonuclease recognition sites for HindIII, BamHI, PstI, SalI, SmaI, BglII, XhoI, SphI and ClaI, respectively.

FixX of *R. trifolii* is a 297 bp DNA sequence encoding 98 amino acid residues as shown in Table 1. It is located as shown in FIG. 1 downstream from the fixC coding region and upstream from the nifA coding region. FixX of *R. meliloti* is a also a 297 bp DNA sequence encoding a 10.1 kD protein having 98 amino acid residues as shown in Table 2, and in a similar location between fixC and nifA (FIG. 2). Table 3 shows a comparison of the amino acid sequences of *R. trifolii* and *R. meliloti* fixX proteins. There are no obvious promoter sequences in the short intercistronic region between fixC and fixX (13 bp in *R. meliloti*; 15 bp in *R. trifolii*). Transcription of the fixX genes in *R. meliloti* and *R. trifolii* is dependent on readthrough transcription of fixC. There is a high degree of homology between the sequences corresponding to fixX in *R. trifolii*, *R. meliloti*, *R. leguminosarum*, and Bradyrhizobium sp. (Paraponia). The location of similar sequences is analogous in other rhizobial species carrying nitrogenase genes on Sym plasmids. The fixX sequences set forth herein as well as sequences having about 75% or 80% to 100% homology thereto are useful for the purposes set forth herein. As more particularly described hereafter, hybridization conditions involving a temperature of about 25° C. below the melting temperature of DNA will identify sequences with a useful degree of homology.

TABLE 1

DNA sequence of 3' end of fixC, 12 bp intergenic region, fixX and portion of intergenic region preceding nifA for *R. trifolii*

CC CGG TGG GGA TTA ATT TCA GAT GCA GTC CGG fixC     ***
CTC GCC CGC GCG TGG CGC TAA AAG GAG ATC →
CAG ATG AAG GCC ATC GTT AAG CGG CGA GTT GAG
    Met Lys Ala Ile Val Lys Arg Arg Val Glu HindIII
GAC AAG CTT TAC CAG AAC CGA TAT CTG GTT GAC
Asp Lys Leu Tyr Gln Asn Arg Tyr Leu Val Asp SmaI
CCG GGC CGT CCA CAC ATA TCG GTC AGA AAA CAC
Pro Gly Arg Pro His Ile Ser Val Arg Lys His CTG TTT CCA ACC CCA AAC CTA ATC GCC TTG ACG
Leu Phe Pro Thr Pro Asn Leu Ile Ala Leu Thr CAA GTG TGT CCG GCG AAA TGC TAT CAG CTG AAC
Gln Val Cys Pro Ala Lys Cys Tyr Gln Leu Asn GAC AGA CGT CAA GTG ATC ATC GTT TCC GAT GGC
Asp Arg Arg Gln Val Ile Ile Val Ser Asp Gly

TABLE 1-continued

DNA sequence of 3' end of fixC, 12 bp intergenic region, fixX and portion of intergenic region preceding nifA for *R. trifolii*

TGC TTG GAA TGC GGG ACA TGC AAC GTG TTA TGC
Cys Leu Glu Cys Gly Thr Cys Asn Val Leu Cys

GGA CCC GAC GGC GAC ATT GAG TGG ACG TAT CCA
Gly Pro Asp Gly Asp Ile Glu Trp Thr Tyr Pro

CGA GGT GGG TTC GGC GTT CTC TTC AAG TTT GGA
Arg Gly Gly Phe Gly Val Leu Phe Lys Phe Gly

***
TGA ACA GCT TCT TCT GTA GTC GAT ACA GCC GTT

CGG TGG CAA ACG CGA GGT AAG CAA ACA A

Arrow indicates fixX ATG start codon.
Asterisks indicate termination signals.
Restriction sites are shown by overline.

TABLE 2

DNA and deduced amino acid sequence of the fixX gene of *R. meliloti*

Met Lys Thr Ala Met Pro Glu Arg Ile Glu
ATG AAG ACG GCA ATG CCG GAG CGT ATC GAA

Asp Lys Leu Tyr Gln Asn Arg Tyr Leu Val
GAC AAG CTT TAC CAG AAC CGC TAT CTG GTC

Asp Ala Gly Arg Pro His Ile Thr Val Arg
GAC GCA GGG CGT CCA CAC ATT ACA GTG CGG

Pro His Arg Ser Pro Ser Leu Asn Leu Leu
CCA CAC CGG TCC CCA AGC TTA AAC CTG CTC

Ala Leu Thr Arg Val Cys Pro Ala Lys Cys
GCG CTC ACG CGA GTC TGC CCG GCC AAA TGC

Tyr Glu Leu Asn Glu Thr Gly Gln Val Glu
TAC GAG TTG AAT GAA ACT GGG CAA GTG GAA

Val Thr Ala Asp Gly Cys Met Glu Cys Gly
GTC ACT GCC GAT GGC TGC ATG GAG TGC GGC

Thr Cys Arg Val Leu Cys Glu Ala Asn Gly
ACA TGC AGA GTG TTG TGC GAG GCA AAC GGT

Asp Val Glu Trp Ser Tyr Pro Arg Gly Gly
GAC GTC GAG TGG AGC TAT CCA CGA GGT GGC

Phe Gly Val Leu Phe Lys Phe Gly
TTC GGT GTC CTC TTC AAG TTC GGA TGA

TABLE 3

Comparison of the amino acid sequences of the *Rhizobium trifolii* (Rt) and *Rhizobium meliloti* (Rm) fixX proteins Rt MET LYS ALA ILE  VAL LYS ARG ARG VAL GLU
Rm MET LYS THR ALA MET PRO GLU ARG ILE  GLU

ASP LYS LEU TYR GLN ASN
ASP LYS LEU TYR GLN ASN

Rt ARG TYR LEU VAL ASP PRO GLY ARG PRO HIS
Rm ARG TYR LEU VAL ASP ALA GLY ARG PRO HIS

ILE SER VAL ARG LYS HIS
ILE THR VAL ARG PRO HIS

Rt LEU PHE PRO THR PRO ASN LEU ILE ALA LEU
Rm ARG SER PRO SER LEU ASN LEU LEU ALA LEU

THR GLN VAL CYS PRO ALA LYS
THR ARG VAL CYS PRO ALA LYS

Rt CYS TYR GLN LEU ASN ASP ARG ARG GLN VAL
Rm CYS TYR GLU LEU ASN GLU THR GLY GLN VAL

TABLE 3-continued

Comparison of the amino acid sequences of the *Rhizobium trifolii*
(Rt) and *Rhizobium meliloti* (Rm) fixX proteins

ILE VAL SER ASP GLY — CYS
GLU VAL THR ALA ASP GLY CYS

Rt LEU GLU CYS GLY THR CYS ASN VAL LEU CYS
Rm MET GLU CYS GLY THR CYS ARG VAL LEU CYS

GLY PRO ASP GLY ASP ILE GLU
GLU ALA ASN GLY ASP VAL GLU

Rt TRP THR TYR PRO ARG GLY GLY PHE GLY VAL
Rm TRP SER TYR PRO ARG GLY GLY PHE GLY VAL

LEU PHE LYS PHE GLY
LEU PHE LYS PHE GLY

Other rhizobial ferredoxin genes which encode proteins having the characteristic cysteine residue pattern are similar in function to FixX in providing electron transport functions to nitrogenase reactions and they are considered equivalent to FixX. Such proteins preferably have about 70% to 100% homology to the sequences shown in Tables 1 and 2.

FixY of *R. meliloti* is a 194 bp DNA sequence encoding a 6.8 kD protein with 64 amino acid residues, as shown in Table 4. It is located in *R. melitoti* as shown in FIG. 2 downstream from the nifB coding region and separated therefrom by an intergenic region of 31 bp. There are no obvious promoter sequences immediately upstream from FixY, and transcription of this gene in *R. melitoti* depends on readthrough transcription from nifA and nifB. FixY-homologous genes are found in analogous positions in other rhizobial species having Sym plasmids. Analogous genes exist in other fast- and slow-growing rhizobia, including *R. leguminosarum* and *R. trifolii*. The FixY sequence set forth herein, as well as sequences having about 75% or 80% to 100% homology thereto, are useful for the purposes set forth herein. Other rhizobial ferredoxin genes which encode proteins having the characteristic cysteine residue pattern, and which are similar in function to FixY in providing electron transport functions to nitrogenase reactions, are considered equivalent to FixY.

TABLE 4

DNA and deduced amino acid sequence of the
fixY gene of *R. meliloti*

Met Ala Phe Lys Ile Ile Ala Ser Gln Cys Thr
ATG GCC TTC AAG ATT ATT GCA TCT CAA TGC ACT

Gln Cys Gly Ala Cys Glu Phe Glu Cys Pro Arg
CAG TGC GGC GCC TGC GAG TTT GAA TGT CCG CGG

Gly Ala Val Asn Phe Lys Gly Glu Lys Tyr
GGG GCG GTC AAT TTC AAA GGC GAG AAA TAC

Val Ile Asp Pro Thr Lys Cys Asn Glu Cys Lys
GTG ATT GAC CCG ACC AAA TGC AAC GAA TGC AAG

Gly Gly Phe Asp Thr Gln Gln Cys Ala Ser Val
GGA GGA TTC GAC ACA CAG CAA TGC GCA TCG GTC

Cys Pro Val Ser Asn Thr Cys Val Pro Ala
TGT CCG GTG TCG AAC ACC TGC GTC CCT GCC TG

Such proteins preferably have about 70% to 100% homology to the amino acid sequence shown in Table 4. Table 5 compares the *R. meliloti* fixY amino acid sequence with that of four other bacterial ferredoxins.

Figure 3:
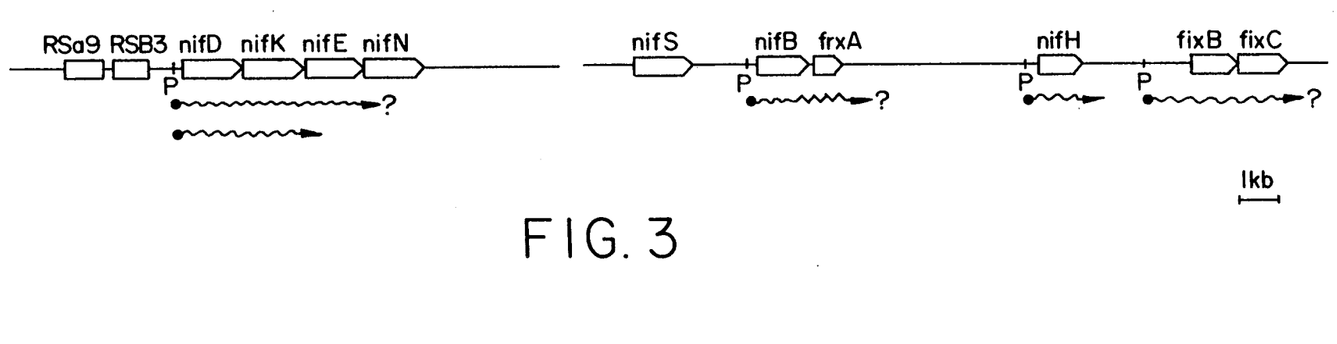
FIG. 3 shows a Region Map of the nif, fix, and frxA genes of cluster 1 of *B. japonicum* (adapted from H. Hennecke et al. (1987) in *Molecular Genetics of Plant-Microbe Interaction*, D. P. S. Verma and N. Brisson (eds.), Martinus Nijhoff Publishers, Dordrecht, The Netherlands, pp. 191–196. Wavy lines indicate transcripts initiated from identified promoters. The question marks at the ends of transcripts denote that transcription termination sites are not known.

FrxA of *B. japonicum* is a 222 bp DNA sequence encoding 74 amino acid residues, as shown in Table 6. From the predicted amino acid sequence, a theoretical molecular weight of 7841 was calculated for the FrxA apoprotein. The frxA gene is located, as shown in FIG. 3, about 13 bp downstream from the nifB coding region. The frxA gene is cotranscribed with nifB. The frxA apoprotein contains the diagnostic pattern of cysteine residues (C--C--C---C). There is significant homology between the *B. japonicum* FrxA amino acid sequence and that of the fixY ferredoxin of *R. meliloti* as shown in Table 7. There is also significant homology between the frxA ferredoxin and ferredoxin I of the photosynthetic bacterium *Rhodopseudomonas palustris* (Table 8). Other rhizobial ferredoxin genes which have 70% or greater homology to the frxA deduced amino acid sequence are considered functionally equivalent thereto.

The ferredoxin genes described above may be isolated from recombinant DNA molecules containing rhizobial DNA or from the rhizobia in which they are found by means known to the art, utilizing pre-existing restriction sites, or utilizing synthetic restriction sites.

TABLE 5

Comparison of the *R. meliloti* fixY amino acid
sequence with four other bacterial ferredoxins.

1. MAFKIIASQCTQCGACEFECPRGAVNFKGEKYVIDPTK
   CNECKGGFDTQQCASVCPVSNTCVPA

2. ALYITEECTYCGACEPECPVTAISAGDDIYVIDANTCN
   ECAGL—DEQACVAVCPAECIVQG

3. ALYITEECTYCGACEPECPTNAISAGSEIYVIDAAGCTE
   CVGFADAPACAAVCPAECIVQG

4. AHRITEECTYCAACEPECPVNAISAGDEIYIVDESVCTD
   CEGYYDEPACVAVCPVDCIIKV

5. MAMAIDGYECTVCGDCKPVCPTGSIVLQGGIYVIDAD
   SCNECADLG—EPRCLGVCPVDFCIQPLD

The amino acid structure predicted from the DNA sequence of
*R. meliloti* fixY gene (1) is compared with amino acid sequences
of the ferredoxins of:
(2) *Chlorobium limicola*,
(3) *Chlorobium limicola f.*,
(4) *Chlorobium limicola* 2, and
(5) *Azotobacter chroococcum*.

Residues identical in the sequences are indicated with bold face type.
The single letter code is used.

TABLE 6

DNA and deduced amino acid sequences of the 3' end of nifB, 13
bp intergenic region, the frxA gene, and a portion of the
downstream intergenic region from *B. japonicum*.

nifB

1470 TGG CCT GGA GAT CGG ATC TCT GCG GCG
     Trp Pro Gly Asp Arg Ile Ser Ala Ala frxA TA<u>A GGAG</u>GAATAT GTG CCA TTC AAA ATC ATC
•                    (Met) Pro Phe Lys Ile Ile GCC TCG CAG TGC
Ala Ser Gln Cys 1540 ACG AGC TGC GCA GCT TGC GAG CCT TTA TGC
     Thr Ser Cys Ser Ala Cys Glu Pro Leu Cys CCG AAC GTT GCT ATT TCG GAG AAG GGG GGA
Pro Asn Val Ala Ile Ser Glu Lys Gly Gly

TABLE 6-continued

DNA and deduced amino acid sequences of the 3' end of nifB, 13 bp intergenic region, the frxA gene, and a portion of the downstream intergenic region from B. japonicum.

```
     AAC TTT GTC
     Asn Phe Val

1609 ATT GAA GCG GCG AAA TGC AGC GAA TTG CGT
     Ile Glu Ala Ala Lys Cys Ser Gly Leu Arg

GGG CAT TTT GAC GAA CCG CAA TGT GCC GCT
     Gly His Phe Asp Glu Pro Gln Cys Ala Ala

GCC TGT CCG
     Ala Cys Pro

1678 GTC GAC AAC ACC TGC GTG GTT GAC AGG GCC
     Val Asp Gln Thr Cys Val Val Asp Arg Ala

TTG CCT CGC TAC CAG GCG CCC GTC TGA AGTG
     Leu Pro Arg Tyr Gln Ala Pro Val  *

TGGACCGTAC
```

The numbering system continues that of J. Noti et al. (1986) J. Bacteriol. 167: 774–783.
The putative Shine-Dalgarno sequence for frxA is overscored and underlined.
Termination signals are indicated by asterisks.

TABLE 7

Comparison of the amino acid sequences of R. meliloti (Rm) fixY and B. japonicum (Bj) frxA proteins Rm MET ALA PHE LYS ILE ILE ALA SER GLN CYS THR
Bj  MET PRO PHE LYS ILE ILE ALA SER GLN CYS THR

GLN CYS GLY ALA CYS GLU PHE
SER CYS SER ALA CYS GLU PRO

Rm GLU CYS PRO ARG GLY ALA VAL ASN PHE LYS
Bj  LEU CYS PRO ASN VAL ALA ILE SER GLU LYS

GLY GLU LYS TYR VAL ILE ASP PRO
GLY GLY ASN PHE VAL ILE GLU ALA

Rm THR LYS CYS ASN GLU CYS LYS GLY GLY PHE
Bj  ALA LYS CYS SER GLU LEU ARG GLY HIS PHE

ASP THR GLN GLN CYS ALA SER VAL
ASP GLU PRO GLN CYS ALA ALA ALA

Rm CYS PRO VAL SER ASN THR CYS VAL PRO ALA
Bj  CYS PRO VAL ASP GLN THR CYS VAL VAL ASP

ARG ALA LEU PRO ARG TYR GLN

Bj ALA PRO VAL suitable bacteria by means known to the art to produce expression products comprising ferredoxin proteins. The term "expression" means transcription of the DNA sequence into RNA and translation of the RNA into amino acid sequences. Methods for the production of gene products are known to the art, and usually involve construction of an expression plasmid comprising the gene to be expressed under the regulatory control of a promoter, insertion of the plasmid into a bacterium in which the plasmid functions, followed by multiplication of the bacterium on a suitable medium, and recovery of the expression product. Iron present in the host cells will complex spontaneously with the sulfurs of the cysteine residues in the apoprotein.

As promoters for the expression of the ferredoxin genes, the regulatory regions controlling these genes in their rhizobial source organisms may be used, as well as other promoters, e.g., RtRS1, the nifH promoter region, as described in patent application Ser. No. 900,270 incorporated herein by reference (and designated RS1 in patent application Ser. No. 662,611 incorporated herein by reference). Other suitable promoters may be selected depending on the host bacteria in which transcription is desired. (See e.g. M. Graves and J. Rabinowitz, J. Biol. Chem. 261:11409; J. L. Wiggs et al. (1979) Cell 16:97–109; J. Beynon et al. (1983) Cell 34:665–671). Preferably the promoter controlling the expression of FixX or fixY in rhizobia is a constitutive promoter expressed in the bacteroid state, e.g., the Km/neo promoter of Tn5, and the promoter controlling the expression of frxA in rhizobia is preferably a constitutive promoter which is expressed in the free-living state, e.g., the Km/neo promoter of Tn5. When expression of a rhizobial ferredoxin gene is desired in a non-rhizobial host, the promoter sequences controlling the expression of said gene will be chosen according to the art pertaining to that host.

Table 1 shows the amino acid sequence of the ferredoxin protein which is the expression product of the fixX gene of R. trifolii. The amino acid sequences of the expression products of other ferredoxin genes may be readily deduced from the DNA sequences of such genes, and all such expression products are useful for the purposes described above. The rhizobial ferredoxin proteins of this invention are preferably prepared as expression products of the ferredoxin sequences described herein, but may also be prepared by means known to the art for synthesizing or purifying proteins of this type. All such similar ferredoxin proteins having the characteristic pattern of cysteine residues and functioning in electron transport as described herein are considered equivalent to the gene expression products

TABLE 8

Comparison of the predicted amino acid sequence of the B. japonicum ferredoxin with other bacterial ferredoxins.

```
              10          20          30          40          50          60          70
               *     *     *           ,·             *           *     *     *

Bj FrxA   MPF KI I ASQCTS CS ACEPL CPNV AIS E KGGNF VIE AAKCS ELRGH FDEPQCAA ACPVDNTCVVDRALPRY-
          | |  |   | |   ||  |          ||| |            |||   |          |    | ||          QAPV
Rp FdI    AY KI I TSQCTVCGA CEFECPNA AIAMKR GT YVIDA VKCTECEGH FDKPQCVA VCPVDNTCVPA
          ||  |   |  ||    |          |||   |            |  ||
Cl FDI    ALYI T EECTYCGA CEPECPVT AIS A GDDI TVIDANT CNECAG—LDEQACVA VCPAECTVQG
          ||| |   | ||    |          |||   |           |    |  ||
Ac FdIII  MAMAI DGYECTVCGDCKP VCPTGS IVL QGGI TVIDADS ENECAD—LGEPR CLGVCPVDFCIQPLDD
```

Comparison of the predicted anion acid sequence of the FrxA protein with ferredoxins (Fd) from R. palustris (Pr), C. limicola (Cl), and A. chroococcum (Ac); for references, see text. Identical amino acids in all four sequences are connected by vertical lines.
The eight cysteines in the B. japonicum (Bj) FrxA protein (*) are indicated. From S. Ebeling et al. (1988) 170: 1999–2001.

They may be combined with other DNA, including suitable promoters and regulatory regions, to form recombinant DNA molecules which may be inserted into described herein. Preferred ferredoxin proteins have the amino acid sequences set forth in Tables 1, 2, 4, and 6, or are proteins having at least 70% amino acid homology to said sequences.

Recombinant constructions using the ferredoxin sequences of this invention may also be useful for enhancing nitrogenase efficiency in rhizobial hosts. In connection with this purpose, it is preferred that the genes be inserted immediately adjacent to their natural counterparts in the organism so as to repeat the natural sequences. It is also preferred that the genes have close to 100% homology to the naturally occurring genes in the organism into which they are placed. Additional regulatory regions including enhancers may be used in such constructions if desired, but are not necessary.

In addition to the foregoing utilities, the sequences of this invention may be used as probes to identify ferredoxin genes, which are equivalent to those claimed herein, in rhizobia or in other organisms, all as known to the art. Preferably, a labelled probe consisting of a sequence of this invention or a partial sequence of this invention is prepared, and a mixture of DNA thought to contain ferredoxin sequences is contacted with the labelled probe. Fragments hybridizing to the probe under conditions of stringency allowing hybridization of sequences with at least about 75% or 80% homology are recovered and isolated and then inserted into suitable expression plasmids for the production of ferredoxins. Partial sequences may also be used as probes, as long as they contain the sequences coding for the characteristic ferredoxin cysteine residue pattern. Such partial sequences used in the probes are referred to herein as "rhizobial ferredoxin diagnostic segments." The skilled artisan will choose probe sequences, preferably about 15-20 nucleotides in length, based on sequence information available from known rhizobial ferredoxin genes. It is noted that a fully degenerate probe for the sequence "cys--cys--" would require an impractically large number of individual oligonucleotides. Hybridization conditions and probe sequence choice will be understood by those skilled in the art.

Source for the rhizobial ferredoxin genes and probes of this invention and equivalent ferredoxin genes include *R. trifolii, R. meliloti, R. leguminosarum, R. phaseoli, R. fredii, R. loti, Bradyrhizobium japonicum,* and Bradyrhizobium sp. (Paraponia). Preferred sources are *B. japonicum, R. trifolii,* and *R. meliloti.* The sequences may be directly derived from rhizobia, or may be synthesized in whole or in part by means known to the art. "Derived from rhizobia" as used herein means directly obtained from rhizobia or prepared from sequence information obtained from rhizobial DNA segments.

The recombinant molecules of this invention comprising rhizobial ferredoxin sequences include the sequences per se, the sequences in combination with suitable regulatory regions, with or without additional DNA sequences, plasmids including rhizobial Sym plasmids and plasmid vectors known to the art, phage vectors, and genomic DNA up to, and including complete chromosomes. RNA molecules encoding the rhizobial ferredoxin sequences are considered equivalent to the DNA sequences described herein.

DETAILED DESCRIPTION OF THE INVENTION

To obtain the rhizobial ferredoxin sequences of this invention, a rhizobium containing such sequences is selected: for FixX or fixY-homologous sequences, preferably a rhizobium in which the ferredoxin genes are encoded on the Sym plasmid, e.g., *Rhizobium trifolii* or *R. meliloti,* and for frxA-homologous sequences, preferably a slow-growing rhizobium, e.g., *Bradyrhizobium japonicum.*

DNA containing the ferredoxin sequences is isolated by means known to the art and digested with appropriate restriction enzymes as known to the art, e.g., BamHI or HindIII, to produce DNA fragments. These DNA fragments are fractionated according to size, preferably by agarose gel electrophoresis, and placed in a medium permitting hybridization to labelled probes and recovery of hybridized fragments. The medium containing the fractionated fragments is then probed with a DNA fragment comprising the DNA sequences of this invention, or partial sequences encoding the characteristic ferredoxin cysteine residue pattern as described above, and fragments hybridizing thereto are isolated and ligated into appropriate expression vectors or into rhizobial DNA for enhancement of nitrogenase activity as described above.

Hybridization conditions leading to the identification of sequences having at least about 75% to 80% homology are preferred. The term homology is used in the art to describe a degree of nucleotide sequence identity between polynucleotides (DNA or RNA). Sequences that are homologous across species boundaries or between functionally similar elements are said to be conserved. The presence of sequence homology or conservation is often used to support a genetic or functional relationship between nucleotide sequences. The degree of homology between polynucleotides is quantitatively determined as a percent homology if sequences are known. In the absence of sequence information for comparison, the presence of homology is preferably determined operationally by hybridization experiments. A single strand of DNA or RNA will bind or hybridize to other single-stranded polynucleotides whose sequences are complementary or partially complementary to its own. The strength of this binding depends on a number of factors including the degree of homology between the sequences, the length of the sequences, the nucleotide composition of the sequences, and the experimental conditions for the hybridization. When hybridization is done under stringent conditions, the temperature and washing conditions of the hybridization experiment are adjusted to minimize hybridization of mismatched sequences. In the absence of sequence information, the stringency of hybridization conditions can be adjusted by the use of appropriate positive and negative controls.

Hybridization experiments are often used as a means of screening DNA fragments for the presence of a particular sequence or for sequences homologous to a DNA probe which is known to contain sequence(s) having a particular function. A number of alternative methods for conducting such experiments are known in the art. Hames and Higgins (eds.) (1985) *Nucleic Acid Hybridization* IRL Press, Oxford, UK, provides a review of applicable hybridization techniques.

As is known to the art, by using well-known, published equations one can predict with confidence (plus or minus 1-3%) the minimum nucleotide sequence homology that will be detectable in a particular hybridization experiment, provided one knows the hybridization conditions used including temperature, cation concentration, and percent formamide (if any), and the length and sequence of the nucleic acid fragment used as a hybridization experiment probe. For DNA-DNA hybridization, the melting temperature (Tm) of perfectly matched DNA duplexes under hybridization conditions can be calculated using the following well-known equation:

$$Tm = 81.5 + 0.41(\%G+C) + 16.6\log(M \text{ cation}) - 650/L - 0.6(\% \text{ (v/v) formamide})$$

where %G+C is the mole percent G+C of the hybridization probe, L is the length in bases of the probe, M is the cation concentration in moles/liter in the hybridization buffer, and the % formamide is the percent formamide used in the hybridization (if any).

Mismatches in DNA duplexes have been found to depress the Tm by an average of 1.1° C. for each percent mismatch as defined as number of unpaired bases/total bases in the duplex×100 (J. Wetmur (1976) Ann. Rev. Biophys. Bioeng. 5:337); and the percent homology detectable in a given hybridization experiment can be calculated using the following equation:

$$Tm - T(\text{hybridization}) = 1.1c(\% \text{ mismatch}) \text{ or}$$

$$\frac{100 - (Tm - T(\text{hybridization}))}{1.1C} = \% \text{ homology}$$

The percent homology is 100% − the percent mismatch. A temperature of about 25° C. below the melting temperature of the DNA is preferred herein.

The probe containing rhizobial ferredoxin sequences used to identify additional rhizobial ferredoxin sequences may be derived from rhizobia by the methods set forth in the examples hereof, or may be chemically synthesized by means known in the art. The probe is preferably a rhizobial diagnostic segment comprising less than a complete ferredoxin gene but encoding the characteristic cysteine residue pattern. Because the amino acids between the cysteine residues and the codon usage for a given amino acid may vary from Rhizobium to Rhizobium, the skilled artisan knows that a degenerate probe must be used to isolate additional rhizobial ferredoxin genes. For example, to find a ferredoxin gene equivalent to the FixX genes of R. trifolii and R. meliloti, one chooses a DNA sequence derived from the nucleotide sequence encoding the ferredoxin diagnostic segment, preferably about 15-20 nucleotides in length, i.e. 18. A representative oligonucleotide can be prepared using the sequence information of the first six codons of the diagnostic segment, after comparing the sequences of the two genes. The second amino acid is either leucine or methionine, encoded by a total of seven theoretical codons. The glutamate and threonine residues at the third position could be encoded by a total of two and four codons respectively.

In order to fully cover all possible codons for the two known amino acid sequences, a 224-fold degenerate probe is required. Cysteine can be encoded by two codons, although in the two named genes, only one is used. There are two possible cysteine codons although only one (TGC) is used in this portion of the two disclosed fixX sequences; if the probe included two cysteine codons at two positions, a 224-fold degenerate probe would be required. One skilled in the art will know how to choose the portion of sequence for probe construction, the fold-degeneracy required to select fragments of DNA carrying rhizobial ferredoxin genes, and the appropriate conditions for performing the hybridization reactions for selecting and identifying said rhizobial ferredoxin genes.

DNA synthesis may be accomplished using well established procedures (i.e., M. Caruthers (1983) in *Methodology of DNA and RNA Sequencing*, Weissman (ed.), Praeger Publishers (New York) Chapter 1), or automated chemical synthesis can be performed using one of a number of commercially available machines. The plasmids containing ferredoxin sequences described in the examples with respect to R. trifolii and R. meliloti are preferred sources of fixX and fixY equivalent ferredoxin genes, and plasmids containing B. japonicum ferredoxin sequences are the preferred sources of frxA-homologous ferredoxin genes. However, the ferredoxin sequences encoded in rhizobial chromosomes or in other plasmids comprising appropriate Sym plasmid segments as known to the art may also be used.

As an alternative to using probes to locate ferredoxin genes, the methods shown in the examples herein describing the sequencing of DNA leading to the original discovery of the ferredoxin sequences claimed herein may be used, with suitable adaptations as known to the art, to isolate, sequence, and characterize additional rhizobial ferredoxin genes, especially with respect to rhizobial genes whose positions relative to fixC, nifA, and nifB are conserved.

To prepare recombinant DNA molecules useful for expressing the ferredoxin genes of this invention to produce ferredoxin proteins, methods known to the art are used. The selected ferredoxin gene is inserted into an expression vector under the regulatory control of a suitable promoter. The term promoter is used in the art to designate the nucleotide sequences adjacent to the 5' end of a structural gene which are involved in the initiation of transcription. Promoters contain DNA sequence elements which ensure proper binding and activation of RNA polymerase, influence where transcription will start, and affect the level of transcription. Further, specific sequences within and adjacent to promoter regions may function in the regulation (induction or repression) of gene expression in response to environmental stimuli or specific chemical species (Ribaud and Schwartz (1984) Ann. Rev. Genet. 18:173-206). The size of promoters is variable. In many cases promoter activity is confined to approximately 200 bp of sequence in the 5' direction from the transcription start site. However, sequences out to approximately 400 bp 5' have been implicated in the regulation of certain genes. The majority of promoters control the initiation of transcription in one direction only, so in order to be under the control of a promoter, a structural gene is usually located downstream (in the 3' direction) of the promoter, and in the correct orientation to the promoter as is well understood in the art. The distance between the promoter and the structural gene is believed to be an important factor in determining the level of gene expression. One or several genes may be under the regulatory control of a single promoter or conversely, one or more promoters may control a single structural gene. Regulatory control refers to the modulation of gene expression by sequence elements upstream of the transcription start site. Regulation may result in an on/off switch for transcription, or it may result in variations in the level of gene expression. To place a gene under the regulatory control of sequence elements means to place it sufficiently close to such sequence elements such that the gene is switched on or off, or such that its expression level is measurably varied.

Suitable hosts for expression vectors are known in the art. *E. coli* is a preferred host. Comparisons of the promoter sequences of a number of *E. coli* genes have revealed conserved sequence elements at −10 (10 nucleotides 5′ to the transcription start site, which is defined as +1) and at −35 (M. Rosenberg and D. Court (1979) Ann. Rev. Genet. 13:319-353). These sequences have been implicated in RNA polymerase binding. An average *E. coli* promoter can be represented by the consensus sequence 5′-TTGACA-----TATAAT-3′. The distance between the two elements of this consensus sequence is generally about 15-19 bp. Promoters with similar sequence elements have been found in the genes of other gram-negative bacteria, but the skilled artisan will understand that all promoters from gram-negative bacteria will not be utilized with equal efficiency (e.g., J. L. Wiggs et al. (1979) Cell 16:97-109). *E. coli* RNA polymerase utilizes Gram-positive promoters efficiently (M. Graves and J. Rabinowitz (1986) J. Biol. Chem. 261:11409). In contrast, eukaryotic promoters have sequence elements that are distinct from the consensus elements of prokaryotic promoters useful in *E. coli*. Eukaryotic promoters are not usually functional in bacteria, and eukaryotic promoters are not generally functional in eukaryotic cells. The skilled artisan understands the proper choice of promoter sequences and host organism.

The term recombinant DNA molecule is used herein to distinguish DNA molecules in which heterologous DNA sequences have been artificially cleaved from their natural sources or ligated together by the techniques of genetic engineering, for example by in vitro use of restriction enzymes or ligase.

The process of cloning a DNA fragment involves excision and isolation of a DNA fragment from its natural source, insertion of the DNA fragment into a recombinant vector and incorporation of the vector into a microorganism or cell wherein the vector and inserted DNA fragment are replicated during proliferation of the microorganism or cell. The term cloned DNA fragment or molecule is used to designate a DNA fragment or molecule produced by the process of cloning and copies (or clones) of the DNA fragment or molecule replicated therefrom.

Except as noted hereafter, standard techniques for cloning, DNA isolation, amplification and purification, for enzymatic reactions involving DNA ligase, DNA polymerase, restriction endonucleases and the like, and various separation techniques are those known and commonly employed by those skilled in the art.

Enzymes are obtained from commercial sources and are used according to the vendors' recommendations or other variations known in the art. Reagents, buffers and culture conditions are also known to the art. References containing standard molecular biological procedures include T. Maniatis et al. (1982) Molecular Cloning, Cold Spring Harbor Laboratory, Cold Spring Harbor, N.Y.; R. Wu (ed.) (1979) Methods Enzymol. 68; R. Wu et al. (eds.) (1983) Methods Enzymol. 100 and 101: L. Grossman and K. Moldave (eds.) (1980) Methods Enzymol. 65; J. Miller (ed.) (1972) *Experiments in Molecular Genetics*, Cold Spring Harbor Laboratory, Cold Spring Harbor, N.Y.; R. Old and S. Primrose (1981) *Principles of Gene Manipulation*, University of California Press, Berkeley, Calif.; R. Schlief and P. Wensink (1982) *Practical Methods in Molecular Biology*; Glover (ed.) (1985) *DNA Cloning*, Vols. I and II, IRL Press, Oxford, U.K.; B. Hames and Higgins (eds.) (1985) *Nucleic Acid Hybridization*; IRL Press, Oxford, U.K.; Setlow and Hollaender (1979) *Genetic Engineering: Principles and Methods*, Vols. 1–4, Plenum Press, New York. Abbreviations and nomenclature, where employed, are deemed standard in the field and commonly used in professional journals such as those cited herein.

EXAMPLES

The following nonlimiting examples are provided for illustrative purposes only and are not intended to limit the scope of the invention.

EXAMPLE 1

*Rhizobium trifolii* strain ANU843 is a wild-type fast-growing Australian isolate (B. Rolfe et al. (1981) *Current Prospectives in Nitrogen Fixation*, A. Gibson et al. (eds.) pp. 142–45). Plasmids Rt578, pRt580, pRt268, pRt602, and pRt585 used in this study were described by P. Schofield et al. (1983) supra. pRt521 contains a 2.6 kb EcoRI Sym plasmid fragment and pRt280 contains an 8 kb BamHI Sym plasmid fragment carrying nodABC and the C-terminal end of nifB. pRt707 is a pUC9 (J. Viera et al. (1982) Gene 19:259-268) derivative with a 2.2 kb HindIII fragment containing the 3′-end of fixX, the entire nifA gene, and the 5′-end of nifB. A selection of these recombinant plasmids were restricted with the appropriate enzymes to liberate the cloned fragments from the pBR328 vector moiety, and separated by electrophoresis through a 1% agarose gel. A Southern blot of this gel was hybridized with a radioactively labelled 4 kb HindIII probe which carried the *R. meliloti* nifA gene (kindly supplied by H. Reilander). Autoradiography of this blot revealed two hybridizing bands corresponding to the 8 kb BamHI insert of pRt280 and the 6.7 ClaI insert of pRt602. The differential hybridization of these two fragments indicated that most of the homology to the *R. meliloti* probe was contained within the ClaI fragment, with the remainder of the homologous DNA sequences being located on the BamHI fragment.

Further analysis of the 6.7 kb ClaI fragment revealed that homology to the *R. meliloti* probe was confined to a 2.2 kb HindIII subfragment (FIG. 2). The DNA sequence of this fragment was determined as described below.

Recombinant plasmid clones were maintained in *E. coli* RR1 (Bolivar et al. (1977) Gene 2:95-113). The sequencing vector M13mp19 (K. Norrander et al. (1983) Gene 26:101-106) was propagated in *E. coli* JPA101.

Plasmid DNA was isolated by cesium chloride centrifugation of cleared lysates as described (J. Watson et al. (1980) Plasmid 4:175-183). DNA manipulations including restriction enzyme digestions, gel electrophoresis, and Southern blot hybridizations were carried out as previously described (P. Schofield et al. (1983) supra). Small scale plasmid DNA isolations for analytical purposes were performed according to the method of D. Holmes et al. (1981) Anal. Biochem. 114:193-197.

The sequence of the 2.2 kb HindIII fragment carrying the *R. trifolii* nifA gene (from pRt707) was determined on both strands, primarily by the chain termination method, using single stranded template DNA derived from M13mp19 clones containing Bal31-gene rated deletions originating from both ends of the fragment. Sequence data were also obtained from M13mp19 recombinant clones carrying Sau3A- or HaeIII-generated subfragments of the 2.2 kb HindIII fragment. The Staden computer program (R. Staden (1984) Nucl. Acids Res. 12:551-567) was used to analyze the DNA sequence of the 2.2 kb HindIII fragment. One complete open reading frame (ORF) was identified as nifA. Immediately upstream of the *R. trifolii* nifA gene is a small ORF of 297 bp. Preceding the translation initiation codon of this ORF is a 15 bp intergenic region and a coding region that shows strong homology to the *R. meliloti* fixC gene (C. Earl et al. (1987) J. Bacteriol. 169:1127-1136). The lack of obvious promoter sequences for this *R. trifolii* ORF suggested that transcription of this gene is dependent on readthrough transcription from the upstream fixC transcription unit. The ORF is cysteine-rich, and the spacing between the cysteine residues is identical to that in ferredoxins from different bacterial genera. The small size of this gene is also consistent with that of ferredoxin genes in other bacterial species. This *R. trifolii* ORF (which we have termed fixX) thus encodes a ferredoxin protein. FixX-homologous sequences were also present in *R. meliloti* and in Bradyrhizobium sp. Parasponia strain ANU289.

EXAMPLE 2

FixX and fixY of *R. meliloti* were mapped as shown in FIG. 3, and were sequenced by analogous methods, specifically using techniques set forth in G. Weber et al. (1985) EMBO J 4:2751-2756. These sequences were obtained from rhizobial DNA cloned in pRmR29D5, as disclosed in G. Ruvkun et al. (1982) Cell 29:551-559. The DNA and the deduced amino sequences are set forth in Tables 2 and 4, and the amino acid sequence of the FixY protein is compared with the sequences of four other bacterial ferredoxins in Table 5.

EXAMPLE 3

Identification of a *Bradyrhizobium japonicum* ferredoxin-like gene

The sequence of the *B. japonicum* nifB gene was published previously (J. Noti et al. (1986) J. Bacteriol. 167:774-783). Upon examination of several hundred base pairs of DNA sequence downstream of nifB (not shown in the above reference), we detected an ORF (termed frxA herein) of 74 codons. That nucleotide sequence and the predicted amino acid sequence of the FrxA protein are disclosed in Table 6. The presumptive GTG start codon is preceded by a well-conserved Shine-Delgarno sequence (AAGGAG) (J. Shine and L. Delgarno (1975) Nature (London) 254:34-38) which overlaps the TAA stop codon of the nifB gene. This suggested translational coupling of nifB and frxA. From the predicted amino acid sequence a theoretical molecular weight of 7841 was calculated for the frxA deduced apoprotein. The frxA amino acid sequence was found to exhibit significant similarity to several published ferredoxin sequences of other bacteria (Table 8). For example, 40 of 63 amino acids of ferredoxin I of *Rhodopseudomonas palustris* (Y. Minami et al. (1984) J. Biochem. 96:585-591), 25 of the 61 amino acids of ferredoxin I of *Chlorobium limicola* (M. Tanaka et al. (1974) Biochem. 13:2953-2959), and 22 of 66 amino acids of ferredoxin III of *Azotobacter chrococcum* (R. Robson et al. (1986) EMBO J. 5:1159-1163) were found at identical positions in the *B. japonicum* FrxA gene. Furthermore, the four cysteine residues near the 5' end of the gene exhibited the diagnostic pattern of cysteine residues of bacterial ferredoxin molecules.

We claim:

1. A recombinant DNA molecule comprising a ferredoxin gene which has the nucleotide sequence of the *Rhizobium trifolii* fixX gene as in Table 1.

2. A recombinant DNA molecule comprising a rhizobial ferredoxin gene which has the nucleotide sequence of the *Rhizobium meliloti* fixX gene as in Table 2.

3. A recombinant DNA molecule comprising a rhizobial ferredoxin gene which has the nucleotide sequence of the *Rhizobium meliloti* fixY gene as in Table 4.

4. A recombinant DNA molecule comprising a rhizobial ferredoxin gene which has the nucleotide sequence of the *Bradyrhizobium japonicum* frxA gene as in Table 6.

* * * * *